US009345515B2

(12) United States Patent
Brunner et al.

(10) Patent No.: US 9,345,515 B2
(45) Date of Patent: May 24, 2016

(54) METHOD OF FIXATING TWO OR MORE ANATOMICAL BODIES

(71) Applicant: DePuy Synthes Products, Inc., Raynham, MA (US)

(72) Inventors: Christian Brunner, Bern (CH); Nico Stohler, Hoelstein (CH); Jens Richter, Basel (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/607,140

(22) Filed: Jan. 28, 2015

(65) Prior Publication Data

US 2015/0134012 A1    May 14, 2015

Related U.S. Application Data

(62) Division of application No. 13/314,528, filed on Dec. 8, 2011, now Pat. No. 8,974,503.

(60) Provisional application No. 61/421,792, filed on Dec. 10, 2010.

(51) Int. Cl.
*A61B 17/68* (2006.01)
*A61B 17/80* (2006.01)
(Continued)

(52) U.S. Cl.
CPC ............... *A61B 17/68* (2013.01); *A61B 17/80* (2013.01); *A61B 17/8605* (2013.01); *A61B 17/00491* (2013.01); *A61B 2017/00004* (2013.01); *A61B 2017/005* (2013.01); *A61B 2017/00526* (2013.01)

(58) Field of Classification Search
CPC ..... A61B 17/80; A61B 17/8605; A61B 17/68
See application file for complete search history.

(56) References Cited

U.S. PATENT DOCUMENTS 5,275,601 A * 1/1994 Gogolewski ....... A61B 17/8052
411/399
5,885,287 A * 3/1999 Bagby ....................... A61F 2/44
623/16.11

(Continued)

FOREIGN PATENT DOCUMENTS

WO    WO 2004/080384 A2    9/2004
WO    WO 2012/078827       6/2012

OTHER PUBLICATIONS

U.S. Appl. No. 61/421,792, filed Dec. 10, 2010, Brunner et al.

*Primary Examiner* — Christian Sevilla
(74) *Attorney, Agent, or Firm* — Baker & Hostetler LLP

(57) ABSTRACT

A method of bone fixation comprises the steps of implanting at least one first fixation element into a respective first anatomical body such that a portion of the first fixation element extends out from an exterior surface of the first anatomical body, and implanting at least one second fixation element into a respective second anatomical body that is adjacent the first anatomical body, such that a portion of the second fixation element extends out from an exterior surface of the second anatomical body. A hardenable material is applied to the portion of each of the fixation elements that extends out from the exterior surface of the respective anatomical body when the hardenable material is in an unhardened state. The hardenable material is hardened such that the hardenable material forms a hardened construct together with the bone fixation elements that bridges the anatomical bodies.

22 Claims, 4 Drawing Sheets

(51) Int. Cl.
*A61B 17/86* (2006.01)
*A61B 17/00* (2006.01)

(56) References Cited

U.S. PATENT DOCUMENTS

| | | | | |
|---|---|---|---|---|
| 5,889,132 | A * | 3/1999 | Rheinberger | A61K 6/093 526/279 |
| 5,895,412 | A * | 4/1999 | Tucker | A61B 17/00491 606/213 |
| 5,941,911 | A * | 8/1999 | Buechel | A61B 17/8605 433/174 |
| 6,425,949 | B1 * | 7/2002 | Lemaitre | A61L 24/0084 106/35 |
| 6,458,868 | B1 * | 10/2002 | Okada | C07F 9/091 523/116 |
| 6,706,273 | B1 * | 3/2004 | Roessler | A61L 24/0063 424/422 |
| 8,221,477 | B2 * | 7/2012 | Aeschlimann | A61B 17/00491 606/281 |
| 8,673,014 | B2 * | 3/2014 | Burke | A61F 2/2875 623/17.16 |
| 8,974,503 | B2 | 3/2015 | Brunner et al. | |
| 2004/0153075 | A1 * | 8/2004 | Roger | A61B 17/68 606/285 |
| 2005/0234453 | A1 * | 10/2005 | Shaolian | A61B 17/1671 606/60 |
| 2006/0142772 | A1 * | 6/2006 | Ralph | A61B 17/866 606/76 |
| 2007/0112428 | A1 * | 5/2007 | Lancial | A61F 2/4405 623/17.12 |
| 2007/0186818 | A1 * | 8/2007 | Bohner | A61L 24/02 106/691 |
| 2007/0265704 | A1 * | 11/2007 | Mayer | A61B 17/0469 623/11.11 |
| 2008/0044374 | A1 * | 2/2008 | Lavergne | A61L 24/0094 424/78.31 |
| 2009/0143780 | A1 * | 6/2009 | Gabele | A61B 17/8033 606/59 |
| 2009/0177226 | A1 * | 7/2009 | Reinprecht | A61L 24/0042 606/214 |
| 2010/0100124 | A1 * | 4/2010 | Calabrese | A61L 24/0042 606/214 |
| 2010/0152854 | A1 * | 6/2010 | Slivka | A61B 17/7071 623/17.12 |
| 2010/0274358 | A1 * | 10/2010 | Mueller | A61B 17/7059 623/17.16 |
| 2012/0150234 | A1 * | 6/2012 | Brunner | A61B 17/80 606/281 |
| 2015/0134012 | A1 * | 5/2015 | Brunner | A61B 17/80 606/286 |

* cited by examiner

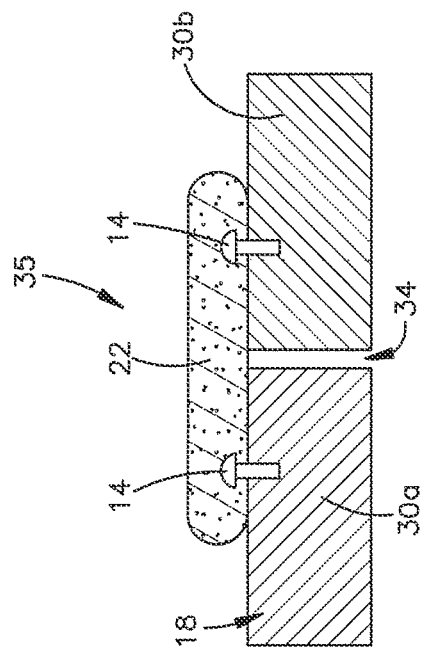
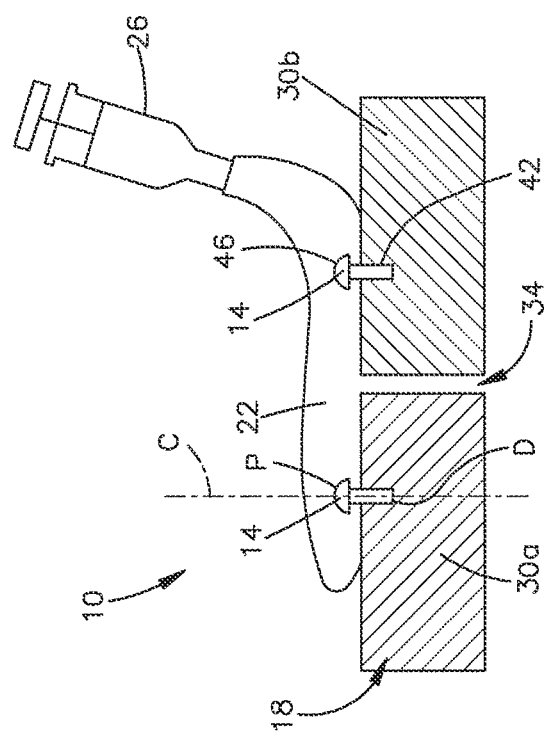

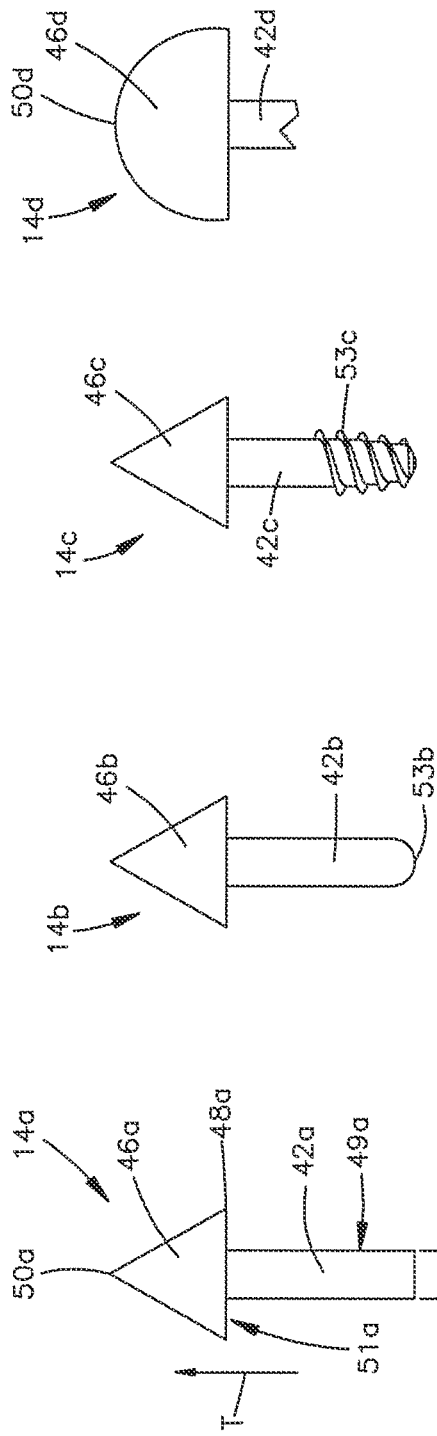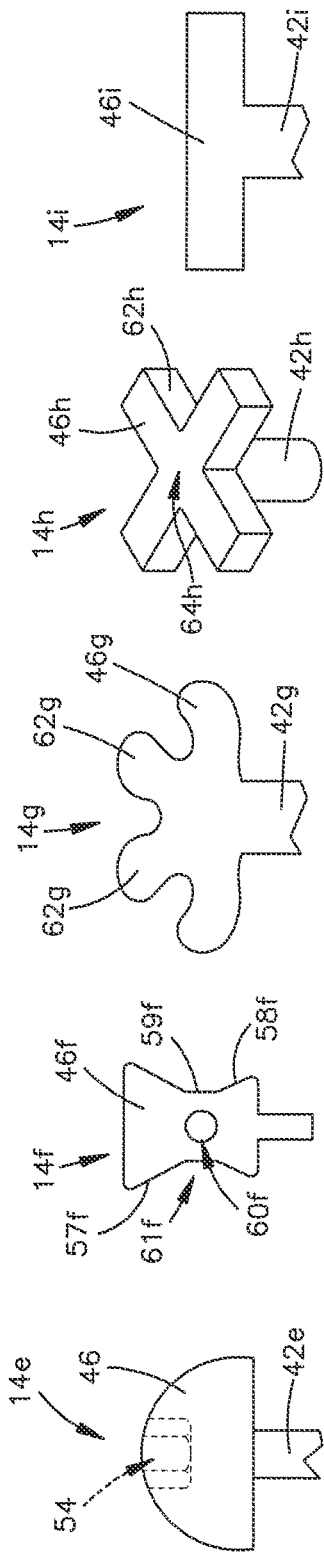

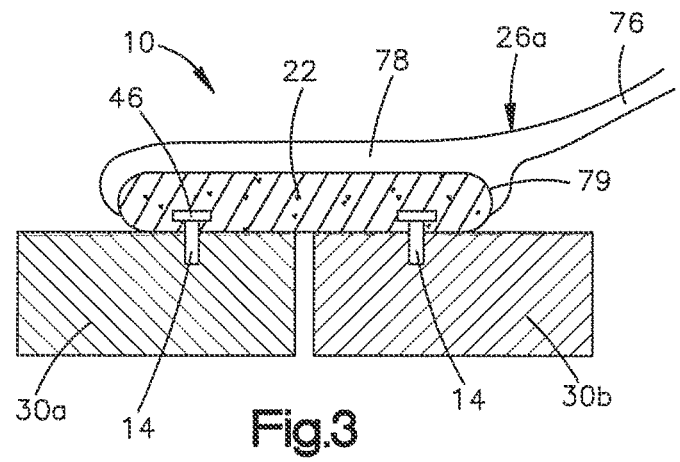
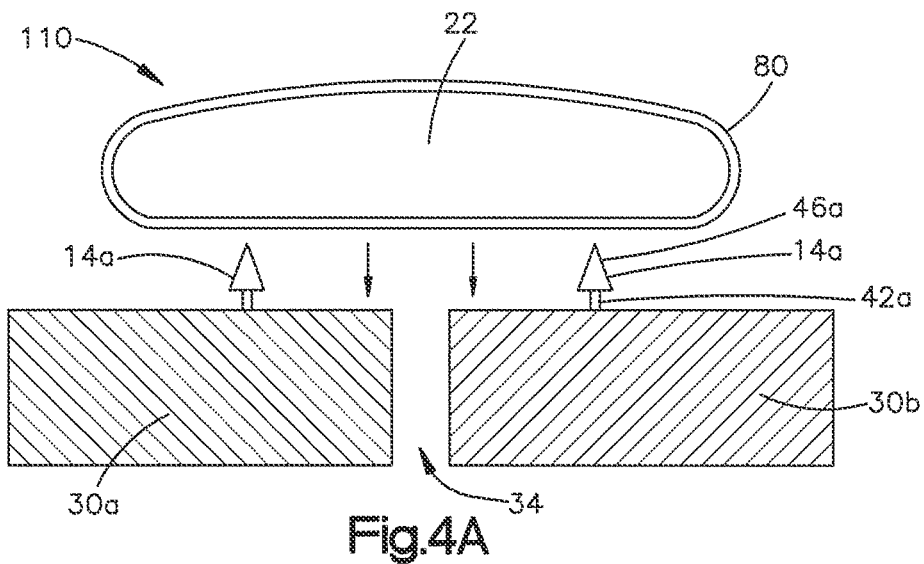
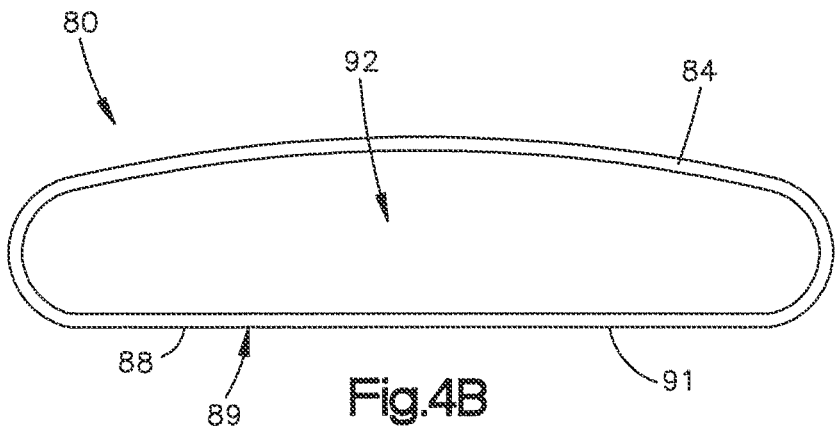

METHOD OF FIXATING TWO OR MORE ANATOMICAL BODIES

CROSS REFERENCE TO RELATED APPLICATIONS

This application is a divisional of U.S. application Ser. No. 13/314,528, filed Dec. 8, 2011, which claims the benefit of U.S. Provisional Application Ser. No. 61/421,792 filed Dec. 10, 2010, the entire contents of each are expressly incorporated herein by reference thereto.

BACKGROUND OF THE INVENTION

Internal fixation of bone fragments on opposite sides of a bone gap, such as a bone fracture, is currently performed using a construct that includes metal plates and screws (e.g. Ti or stainless steel). Typically, holes are drilled in each bone fragment according to the design/geometry of the plate. The plate is then fixed to the bone fragments using the screws. Although state-of-the-art, this procedure has the disadvantage of being limited to the plate design when drilling the holes for fixation of the construct.

BRIEF SUMMARY OF THE INVENTION

In accordance with one embodiment, a method of bone fixation comprises the steps of implanting at least one first fixation element into a respective first anatomical body such that a portion of the first fixation element extends out from an exterior surface of the first anatomical body, and implanting at least one second fixation element into a respective second anatomical body that is adjacent to the first anatomical body, such that a portion of the second fixation element extends out from an exterior surface of the second anatomical body. A hardenable material is applied to the portion of each of the fixation elements that extends out from the exterior surface of the respective anatomical body when the hardenable material is in an unhardened state. The hardenable material is hardened such that the hardenable material forms a hardened construct together with the bone fixation elements that bridges the anatomical bodies.

In accordance with another embodiment, a fixation system configured to affix a relative position between first and second anatomical bodies is provided. The system comprises a first fixation element, a second fixation element, and a hardenable material. The first fixation element includes a first shaft that is elongate along a first central axis and a first head that extends proximally from the first shaft. The first shaft is configured to be attached to the first anatomical body. Each of the first shaft and the first head define respective outer dimensions along a direction substantially perpendicular to the first central axis, and the outer dimension of the first head is greater than the outer dimension of the first shaft. The second fixation element includes a second shaft that is elongate along a second central axis and a second head that extends proximally from the second shaft. The second shaft is configured to be attached to the second anatomical body. Each of the second shaft and the second head define respective outer dimension along a direction substantially perpendicular to the second central axis, and the outer dimension of the second head is greater than the outer dimension of the second shaft. The hardenable material is configured to be applied in an unhardened state in a first gap defined between the first head and an exterior surface of a first anatomical body, and further configured to be applied in the unhardened state in a second gap defined between the second head and an exterior surface of the second anatomical body when the first and second shafts are attached to the first and second anatomical bodies. The hardenable material is configured to be hardened so as to join the first and second heads together, thereby fixing a relative position between the first and second anatomical bodies when the first and second shafts are attached to the first and second anatomical bodies, respectively.

In accordance with another embodiment, a fixation system configured to affix a relative position between first and second anatomical bodies is provided. The system comprises a first fixation element configured to be affixed to a first anatomical body, a second fixation element configured to be affixed to a second anatomical body, a hardenable material, and a sheath. The sheath defines a cavity that retains the hardenable material in a non-activated state. The sheath defines a bone-facing surface that has at least one region configured to abut at least one of the first and second fixation elements, wherein the at least one of the first and second fixation elements is configured to rupture the region when pressure is applied to the sheath so as to cause the hardenable material to flow from the cavity through the bone-facing surface and to the first and second fixation elements. The hardenable material is configured to be hardened so as to join the first and second fixation elements together, thereby fixing a relative position between the first and second anatomical bodies.

A BRIEF DESCRIPTION OF THE DRAWINGS

The foregoing summary, as well as the following detailed description of preferred embodiments of the application, will be better understood when read in conjunction with the appended drawings. For the purposes of illustrating the methods and systems of the present application, there is shown in the drawings preferred embodiments. It should be understood, however, that the application is not limited to the precise methods and systems shown. In the drawings:

FIG. 1A is a schematic view of a bone fixation system according to an embodiment, the bone fixation system including a pair of bone fixation elements that are each affixed to a respective bone fragment, a hardenable material, and an application device that applies the hardenable material to the bone fixation elements to thereby fix the two bone fragments relative to each other;

FIG. 1B is a schematic view of the bone fixation system of FIG. 1A after the hardenable material has been cured or otherwise activated so as to harden around at least a portion of the bone fixation elements to form a construct;

FIG. 2A is a side elevation view of a bone fixation element according to an embodiment, the bone fixation element having a shaft, and a head that extends from the shaft and defines a tip at a proximal end;

FIG. 2B is a side elevation view of a bone fixation element according to another embodiment, the bone fixation element having a shaft that defines a rounded distal end;

FIG. 2C is a side elevation view of a bone fixation element according to another embodiment, the bone fixation element having a shaft that defines threads;

FIG. 2D is a side elevation view of a bone fixation element according to another embodiment, the bone fixation element having a head that defines a blunt or otherwise rounded proximal end;

FIG. 2E is a side elevation view of a bone fixation element according to another embodiment, the bone fixation element having a head that defines an engagement feature configured to mate with a mating feature of a driving instrument;

FIG. 2F is a side elevation view of a bone fixation element according to another embodiment, the bone fixation element having a head that defines a passageway configured to receive the hardenable material;

FIG. 2G is a side elevation view of a bone fixation element according to another embodiment, the bone fixation element having a head that defines a plurality of irregular protrusions;

FIG. 2H is a side elevation view of a bone fixation element according to another embodiment, the bone fixation element having a head that defines a cross;

FIG. 2I is a side elevation view of a bone fixation element according to another embodiment, the bone fixation element having a head that defines a flat proximal end;

FIG. 3 is a schematic side sectional view of an application device in accordance with another embodiment, the application device including a syringe and a hood coupled to the syringe and configured to form the hardenable material into a desired shape as the hardenable material is applied to the bone fixation elements;

FIG. 4A is a schematic side sectional view of a bone fixation system according to another embodiment, the system including a sheath containing a hardenable material, the sheath being pressed against bone fixation elements so as to cause the sheath to rupture and the hardenable material to flow around the fixation elements;

FIG. 4B is a schematic side sectional view of the sheath shown in FIG. 4A;

Figure 6A:
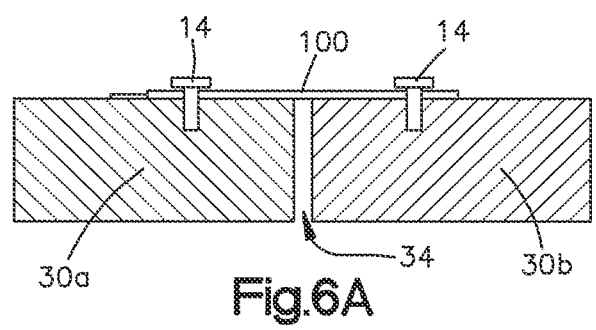
Figure 6B:
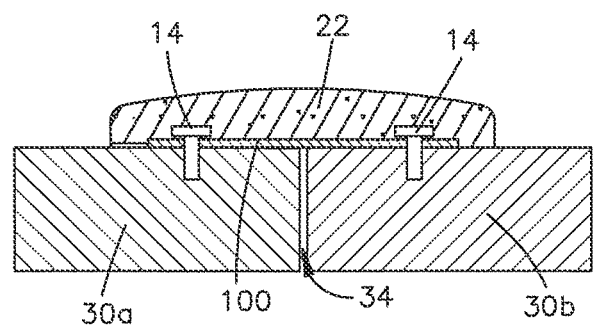

FIG. 6A is a schematic side view of the bone fixation system shown in FIG. 1A further including a reduction instrument such as a wire that is configured to reduce the bone fracture; and FIG. 6B is a schematic side view of the bone fixation system shown in FIG. 6A, after the bone fracture has been reduced, and the hardenable material has been activated to form a construct with the bone fixation elements.

DETAILED DESCRIPTION OF THE INVENTION

Referring to FIGS. 1A and 1B, a bone fixation system 10 includes one or more bone fixation elements 14 that are configured to attach to first and second anatomical bodies 18, a hardenable material 22 that is to be applied to both the anatomical bodies 18 and the fixation elements 14, and an application device 26 that is configured to apply the hardenable material 22 to the anatomical bodies 18 and the fixation elements 14. It should be appreciated that the anatomical bodies 18 can each be configured as a bone fragment, soft tissue, implant, or any alternative structure configured to be attached to another anatomical body. In accordance with the illustrated embodiment, first and second anatomical bodies 18 are configured as first and second bone fragments 30a and 30b, separated by a bone gap, such as a fracture 34. It should be appreciated, however, that the gap defined between the first and second anatomical bodies can be defined by conditions other than fractures, including anatomical deformities and gaps defined between implants and bones or soft tissue. As shown, the fixation elements 14 are inserted into the bone fragments 30a and 30b on both sides of the bone gap. The hardenable material 22 may then be applied across the fracture 34 using the application device 26 to thereby bridge the fixation elements 14 on both sides of the fracture 34.

The hardenable material 22 is applied while in a non-activated state. That is, the hardenable material is applied while in an unhardened state so that it may flow around the fixation elements 14 and conform to the surface of the bone fragments 30a and 30b. Subsequently, the hardenable material 14 is cured or otherwise activated in situ by a suitable curing procedure, to polymerize and thereby form a stabilized construct 35. In this way, the hardenable material may be considered a curable implant that is configured to affix first and second fixation elements and thus first and second anatomical bodies relative to each other.

The bone fixation system 10 allows for bone fixation element placement on either side of the fracture independent of the design of a plate geometry. The fracture can then be stabilized by applying the hardenable material 22 that can be subsequently cured to a rigid construct. The hardenable material while in the unhardened state form will adjust to the underlying anatomy.

As shown in FIGS. 1A and 1B, the bone fixation elements 14 may be configured as bone screws, bone pins or bone tacks. The bone fixation elements 14 may be made from a biocompatible material such as Ti, Ti alloys, stainless steel, ceramic or a resorbable material. Each fixation element 14 includes a shaft 42 and a head 46 extending from the shaft 42. The bone fixation element 14 defines a distal end D, a proximal end P, and a central axis C that extends along a transverse direction T from the proximal end P to the distal end D. The bone fixation elements 14 are configured to be affixed to respective bone fragments such that a portion of each bone fixation element extends from a surface of the bone fragment. It should be understood that while the fixation element 14 is described as having a head 46, the fixation element 14 may be devoid of a head 46 and the shaft 42 may be toothed, or otherwise textured as desired so as to define a mechanical interference with the hardenable material after it hardens. As shown in FIGS. 2A-2I, the bone fixation elements 14 may have a variety of features and configurations.

According to an embodiment and in reference to FIG. 2A, a bone fixation element 14a includes a shaft 42a and a head 46a. The shaft 42a is configured to be attached to or otherwise anchored, for instance inserted, in an underlying anatomical structure such as bone, and the head 46a is configured to be anchored in the hardening material 22. The shaft 42a is elongate in the transverse direction T and is cylindrical. The shaft 42a has a smooth outer surface 49a and is configured to be pressed into a pre-drilled hole. The head 46a extends proximally from the shaft 42a and defines a base 48a and a proximal tip 50a. As shown, the head 46a angles or otherwise tapers inward from the base 48a and terminates at the proximal tip 50a. The head 46a is configured to define a mechanical interference with the hardenable material 22 after it hardens.

As shown in FIG. 2A, the shaft 42a has a first dimension $d_1$, such as a diameter, and the head 46a has a second dimension $d_2$, such as a diameter, that is greater than the first dimension $d_1$. In the illustrated embodiment, the base 48a of the head 46a defines the second dimension $d_2$. Because the base 48a has a greater dimension than the shaft 42a, the base 48a defines a shoulder 51a. When the bone fixation element 14a is affixed to a bone fragment, a portion of the bone fixation element 14a that includes a proximal portion of the shaft 42a and the head 46a extends from the bone fragment such that a gap is defined between the surface of the bone fragment and the shoulder 51a. When the hardenable material 22 is applied to the bone fixation element 14a, the hardenable material will flow into the gap and thus under the shoulder 51a. It should be understood, however, that the bone fixation element 14a can be affixed to a bone fragment such that only the head 46a extends from the bone fragment.

It should be understood that the bone fixation element 14*a* and in particular the shaft 42*a* and the head 46*a* of the bone fixation element 14*a* may have other shapes and configurations as desired, for example as shown in FIGS. 2B-2I. Moreover, as shown in FIGS. 2B-2I, the shaft 42*a* and/or the head 46*a* of the fixation element 14*a* may include additional structure as desired. Therefore, the bone fixation elements shown in FIGS. 2B-2I are identical to the bone fixation element 14*a* shown in FIG. 2A unless otherwise described.

In another embodiment and in reference to FIG. 2B, a bone fixation element 14*b* includes a shaft 42*b* that defines a rounded distal end 53*b*. The rounded distal end 53*b* allows the shaft 42*b* to be more easily guided into the pre-drilled hole when the bone fixation element 14*b* is being affixed to the bone fragment. The bone fixation element 14*b* is otherwise identical to the bone fixation element 14*a* shown in FIG. 2A.

In another embodiment and in reference to FIG. 2C, a bone fixation element 14*c* includes a shaft 42*c* that defines an external thread 53*c*. The bone fixation element 14*c* may be self tapping and may be configured to be screwed into the bone fragment. As the bone fixation element 14*c* is screwed or otherwise driven into the bone fragment the thread 53*c* will engage the bone fragment to thereby securely affix the bone fixation element 14*c* to the bone fragment. The bone fixation element 14*c* is otherwise identical to the bone fixation element 14*a* shown in FIG. 2A.

In another embodiment and in reference to FIG. 2D, a bone fixation element 14*d* includes a head 46*d* that is blunt or otherwise defines a rounded proximal end 50*d*. The bone fixation element 14*d* is otherwise identical to the bone fixation element 14*a* shown in FIG. 2A.

In another embodiment and in reference to FIG. 2E, a bone fixation element 14*e* includes a head 46*e* that defines a mating feature 54*e* configured to mate with a corresponding mating feature of a driving instrument. The mating feature 54*e* may allow for further tightening of the fixation element 14*e* before or after curing of the hardenable material 22. In the illustrated embodiment, the mating feature 54*e* is a hexagonal recess 55*e*, though it should be understood that the mating feature 54*e* may include other configurations as desired. The bone fixation element 14*e* is otherwise identical to the bone fixation element 14*a* shown in FIG. 2A.

In another embodiment and in reference to FIG. 2F, a bone fixation element 14*f* includes a head 46*f* that has an upper portion 57*f*, a lower portion 58*f*, and a middle portion 59*f* between the upper and lower portions 57*f* and 58*f*. The upper and lower portions 57*f* and 58*f* each taper inward toward the middle portion 59*f* to thereby define a recess 61*f* that is configured to receive the hardenable material 22. The head 46*f* further has a passageway 60*f* that extends through the middle portion 59*f* along a direction that is transverse to the central axis of the bone fixation element 14*f*. The passageway 60*f* can extend completely through the middle portion 59*f* or may extend partially into the middle portion 59*f* to thereby define a recess. The passageway 60*f* is configured to receive the hardenable material 22 to thereby improve the stability of the construct after the hardenable material 22 has been activated or otherwise cured. It should be understood that the passageway may define other structure, so long as the passageway can receive the hardenable material. For example, the passageway 60*f* may be a hole, a recess, a cavity, or perforations into which the hardenable material can penetrate. Moreover, it should be understood that the passageway 60*f* can extend through any portion of the head 46*f* such as the upper and lower portions 57*f* and 58*f*. The bone fixation element 14*f* is otherwise identical to the bone fixation element 14*a* shown in FIG. 2A.

In another embodiment and in reference to FIG. 2G, a bone fixation element 14*g* includes a head 46*g* having a plurality of protrusions 62*g*. As shown, the protrusions 62*g* can be irregularly shaped and can extend in multiple directions relative to the central axis of the bone fixation element 14*g*. The protrusions 62*g* may be configured to improve the stability of the construct after the hardenable material 22 has been activated or otherwise cured. It should be understood, that the protrusions 62*g* can extend from the central axis such that the protrusions 62*g* are parallel or perpendicular to each other. For example, as shown in FIG. 2H, a bone fixation element 14*h* includes a head 46*h* having protrusions 62*h* that define a cross 64*h*. The bone fixation elements 14*g* and 14*h* are otherwise identical to the bone fixation element 14*a* shown in FIG. 2A.

In another embodiment and in reference to FIG. 2I, a bone fixation element 14*i* includes a head 46*i* that is substantially flat and disc like. It should be understood, however, that the head 46*i* can have other shapes. For example, the head 46*i* may be square shaped, or any other shape as desired. The bone fixation element 14*i* is otherwise identical to the bone fixation element 14*a* shown in FIG. 2A The hardenable material 22 is configured to be applied to the anatomical bodies and the fixation elements 14 in a non-activated state or otherwise unhardened state. That is, the hardenable material 22 may be unhardened, for instance in liquid form, or otherwise have a viscosity that allows the material to flow onto and around the fixation elements 14. For example, the hardenable material 22 may have a viscosity that is between about 10 pascal-second (Pa s) and about 100 Pa s, and preferably between about 30 Pa s and about 60 Pa s. The viscosity of the hardenable material may also be high enough to allow the material to be formed manually (putty-like). For example, in embodiments where the hardenable material has a putty-like or moldable form the hardenable material has a viscosity that is between about 100 Pa s and about 1000 Pa s, and preferably between about 500 Pa s and about 800 Pa s. Subsequently, the hardenable material 22 is configured to be hardened. For example, the hardenable material can harden after a certain period of time or the hardenable material can be cure or otherwise activated to thereby harden the material 22. The hardenable material 22 may be biocompatible, and it may be resorbable or it may be non-resorbable.

The hardenable material 22 may comprise as a base material: bisphenol A diglycidyl methacrylate (Bis-GMA), diglycidylmethacrylate (DGMA), triethyleneglycoldimethacrylate (TEGDMA), urethane dimethacrylate (UDMA), 1,10-decanediol dimethacrylate, 2-hydroxyethylmethacrylate (HEMA), 2-hydroxypropylmethacrylate, ethylene glycol dimethacrylate, diethylene glycol dimethacrylate, tetraethylene glycol dimethacrylate, 1,6-hexamethylene diisocyanate, 1,6-hexanedioldimethacrylate, preferably acryl- or methacryl-based formulations (non-resorbable), vinylester-, vinylcarbonate-, vinylcarbamate-, vinylalcohol-based (resorbable), polycaprolactone (PCL), PCL/tricalciumphosphate (TCP), PCL/hydroxyapatite (HA), polyurethane or any of these materials reinforced with fibers or particles comprising Mg, polylactic acid (PLA), TCP or HA. The hardenable material may further comprise photoinitiators, such as camphorquinone, any ketone or alpha-diketone compounds. The hardenable material may further comprise fillers/additives, such as tricalcium phosphate (TCP). In some embodiments the hardenable material 22 is not composed of methyl methacrylate.

Furthermore, the properties of the chosen initiator system may determine the kinetics of the curing reaction. That is, the hardenable material 22 may also include one or more monomers or comonomers which can be triggered or otherwise activated to polymerize the hardenable material 22 chemically, biochemically or physically. For example, the hardenable material 22 may be activated chemically or biochemically with chemically reactive components, a change in pH of the environment, and reactive biological compounds. The hardenable material may be activated physically with electromagnetic radiation, phase transition, and light activation. It is possible to use one-component hardenable materials. If the hardenable material 22 is radiation-curable, the material 22 may include a biocompatible radiation-sensitive, (i.e. photoinitiator) system. If the hardenable material 22 is temperature curable, the material 22 may contain a temperature-sensitive initiator. If the hardenable material 22 is moisture-curable, the material 22 may contain a water-sensitive initiator. If the hardenable material is pH-change-curable, the material 22 may contain an initiator sensitive to change in pH. The hardenable material 22 may also be applicable at an elevated temperature (<70° C.) and may crystallize at body temperature. Therefore, the activation mechanisms for the hardening material 22 may include electromagnetic radiation, temperature, moisture, pH change, protein-protein interaction, or crystallization. Though it should be understood that the hardening material 22 may be activated using any known mechanism as desired.

The hardenable material 22 may also have certain visual characteristics. For example, the hardenable material may be transparent to visible and/or UV light. The hardenable material may also contain appropriate contrast chemicals (molecules, colloids, particles) so as to improve visibility in X-ray, CT or MRI scans.

In one embodiment the hardenable material 22 may include urethane dimethacrylate (UDMA); bisphenol A diglycidyl methacrylate (Bis-GMA); 1,10-decanediol dimethacrylate (D3MA); photoinitiator system; filler materials (to adjust viscosity) such as cellulose acetate butyrate (ca. 5%) and calcium phosphate powder (e.g. beta-tricalciumphosphate (TCP), hydroxyapatite (HA)) (up to 100 wt. % in base formulation). Such a material may be placed around fixation elements 14 on each side of the fracture 34 and then light-cured with a commercially available blue-light lamp for ca 10 s.

In one embodiment the hardenable material 22 may include one or more anti-inflammatory agents. Non-limiting examples include non-steroidal anti-inflammatory drugs (NSAIDs) such as indomethacin, aspirin, diclofenac sodium, ketoprofen, ibuprofen, mefenamic acid, azulene, phenacetin, isopropylantipyrin, acetaminophen, benzydamine hydrochloride, phenylbutazone, flufenamic acid, mefenamic acid, sodium salicylate, choline salicylate, sasapyrine, clofezone or etodolac; and steroidal drugs such as dexamethasone, dexamethasone sodium sulfate, hydrocortisone and prednisolone.

In one embodiment the hardenable material 22 may include one or more antibacterial and/or antifungal agents. Non-limiting examples include penicillin, ampicillin, amoxicillin, cefalexin, erythromycin ethylsuccinate, bacampicillin hydrochloride, minocycline hydrochloride, chloramphenicol, tetracycline, erythromycin, fluconazole, itraconazole, ketoconazole, miconazole, terbinafine; nlidixic acid, piromidic acid, pipemidic acid trihydrate, enoxacin, cinoxacin, ofloxacin, norfloxacin, ciprofloxacin hydrochloride, silver, iodine and sulfamethoxazole trimethoprim.

In one embodiment the hardenable material 22 may include one or more anti-viral agents. Non-limiting examples include trisodium phosphonoformate, didanosine, dideoxycytidine, azido-deoxythymidine, didehydro-deoxythymidine, adefovir dipivoxil, abacavir, amprenavir, delavirdine, efavirenz, indinavir, lamivudine, nelfinavir, nevirapine, ritonavir, saquinavir and stavudine.

In one embodiment the hardenable material 22 may include an analgesic. Non-limiting examples include codeine, dihydrocodeine, hydrocodone, morphine, dilandid, demoral, fentanyl, pentazocine, oxycodone, pentazocine and propoxyphene.

In one embodiment the hardenable material 22 may include one or more osteoinductive agents that promote and/or induce bone formation. Non-limiting examples include demineralised bone and growth factors such as bone morphogenetic protein ("BMP") including BMP-2 and BMP-7, basic fibroblast growth factor (bFGF), Epogen®, granulocyte colony-stimulating factor (G-CSF), Interleukin growth factor (IGF)-1, osteogenic protein (OP-1), platelet-derived growth factor (PDGF), stem cell proliferation factor (SCPF), recombinant human interleukin (rhIL), transforming growth factor beta (TGFβ) and TGFβ-3.

Referring back to FIG. 1A, the application device 26 can be a syringe adapted to the viscosity of the hardenable material 22 formulation. The application device 26 may also be a glue-gun. If the hardenable material is to be cured using light, the device 26 may also include a light source to instantly cure the material 22. The application device 26 may also be simultaneously used as a repositioning tool to reduce the fracture.

In another embodiment and in reference to FIG. 3 an application device 26a may include a cap/cover or hood in order to confine the area where the hardenable material 22 is deposited and therefore define the shape of the construct. As shown, the application device 26a includes a cannulated portion 76 that extends from a hood portion 78. The cannulated portion 76 defines a cannula that extends into the hood portion 78. The hood portion 78 defines a cavity 79 that is configured to contain the hardenable material 22 and define the shape of the construct after the hardenable material 22 has been cured. As shown, the cannulated portion 76 and the hood portion 78 together define a spoon shaped device that may be placed over the bone fixation elements 14. Once placed, the hardenable material 22 may be injected through the cannula of the cannulated portion 76 and into the cavity 79 of the hood portion 78. The hardenable material 22 may then be cured and the device 26a may be removed. It should be understood, however, that while the application devices 26 and 26a are illustrated as a syringe with a hood or by itself, the application devices 26 and 26a may be any device capable of placing the hardenable material over the fracture and bone fixation elements 14. For example, the application device may be a pistol or pen type instrument or the hardenable material may be applied by hand if for example in a highly viscous state.

In operation and referring back to FIGS. 1A and 1B, the fixation elements 14 are inserted into the bone fragments 30a, and 30b on both sides of the fracture 34. The fixation elements 14 may be inserted into the bone fragments such that a portion of the fixation elements 14 extends or otherwise protrudes from the bone fragment surfaces. In the illustrated embodiment, the fixation elements 14 are inserted into the bone fragments such that a portion of the shafts 42 and the heads 46 extend or otherwise protrude from the bone fragment surfaces. The hardenable material 22 while in a non-activated (liquid state) is then applied using the application device 26, 26a or other application device over the heads 46 of the fixation elements 14. The hardenable material 22 is applied on the heads 46 across the fracture to bridge the two heads 46 on both sides of the fracture 34. In the illustrated embodiment, the heads 46 are embedded within the hardenable material and therefore fully encapsulated by the hardenable material. Subsequently, the hardenable material 22 is cured or otherwise activated in situ by a suitable curing procedure (i.e. time, UV or visible light, laser light of appropriate wavelength, temperature or moisture or other desired method) to polymerize and thereby form a stabilized construct 70. During polymerization of the hardenable material 22, the fracture 34 may be reduced due to the shortening of intramolecular distances and thus shrinkage of the hardenable material 22. Once hardened, the first and second fixation elements and thus the first and second bone fragments will be fixed relative to each other.

In some embodiments, the hardenable material 22 may be applied such that the heads 46 of the fixation elements 14 are not fully covered by the material 22. Subsequently after the material 22 is applied, the material 22 is rendered rigid by curing it. The fixation elements 14 that are not completely inside the hardened or cured material 22, and whose heads 46 are accessible, may be used to further press the construct to the bone by tightening the fixation elements 14 with a driver.

In some embodiments, the hardenable material 22 is applied first and then the bone fixation elements 14 are driven into the bone fragments through the hardenable material. The bone fixation elements 14 may be inserted to a depth that the heads 46 are submerged, or the heads 46 are spaced from the hardenable material 22, or the bone fixation elements 14 can be devoid of heads 46. Once the fixation elements 14 are implanted, the hardenable material may be cured.

In another embodiment and in reference to FIG. 4A, a bone fixation system 110 may include an application device that defines a sheath 80 that is configured to enclose the hardenable material 22 while the hardenable material 22 is in a non-activated state. The sheath 80 may have a maximum transverse height $H_1$ between about 2 mm and about 3 mm. It should be understood, however, that the sheath 80 may have any height, as desired. As shown, the system 110 further includes bone fixation elements (i.e. bone fixation elements 14a) that are configured to rupture the sheath 80 when the sheath 80 is pressed against the heads of fixation elements. When the sheath 80 ruptures the hardenable material 22 will flow onto the bone fragments and around the bone fixation elements 14a.

As shown in FIG. 4B, the sheath 80 includes a sheath body 82 that defines an upper portion 84 and an opposed lower portion 88. The lower portion 88 defines a lower or bone-facing surface 89 of the sheath body 82, and has at least one weakened region 91 that is configured to be pressed onto the bone fixation elements 14 and is suitable for bone contact. For instance, the lower portion 88 can be pressed onto the respective heads 46a of the bone fixation elements 14a. Alternatively, the bone fixation elements 14a can be devoid of heads as desired, and the sheath 80 may be pressed against the shafts 42a of the fixation elements 14a. The sheath 80 may exhibit a mechanical strength sufficient to remain tight when filled with the hardenable material 22 but allowing penetration of the fixation element heads 46a when pressed on. It should be appreciated that while the illustrated embodiment includes a single weakened region, the sheath may include two or more weakened regions that are configured to be punctured by the fixation elements.

Figure 5:
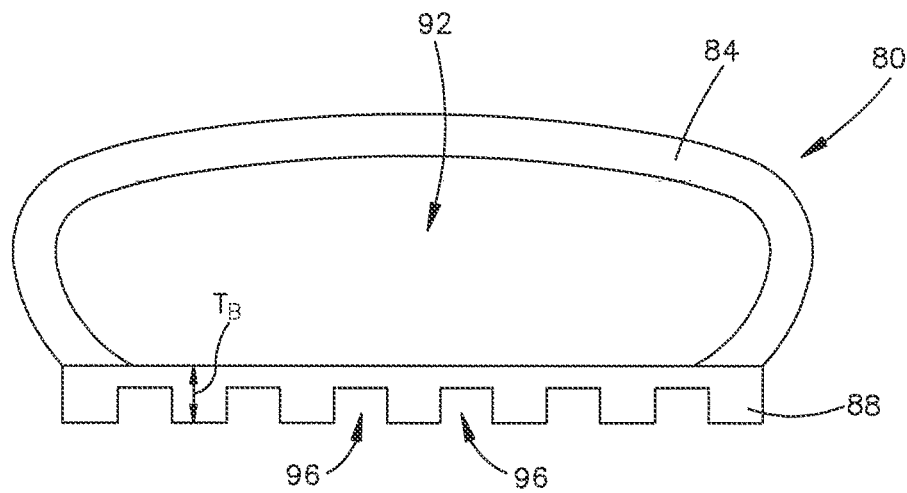
FIG. 5 is a schematic side sectional view of a sheath according to another embodiment, the sheath having a lower portion that defines a plurality of recesses that weaken the lower portion.

The sheath body 82 can define an internal cavity 92. For instance the upper and bottom portions 84 and 88 can enclose the sheath body 82 so as to define the cavity 92. It should be understood that the sheath body 82 can be a unitary structure or multiple parts that are attached to each other. The hardenable material 22 in its non-activated state may be filled into the cavity 92 and sealed within the sheath 80. The sheath 80 may be made from an elastic biocompatible material (resorbable or non-resorbable). The upper portion 84 may be made of a transparent elastomer material and the lower portion 88 or at least the weakened region 91 of the lower portion 88 may be made of a penetrable material such as a cellulose or silk based material or a stiffer thin foil or a brittle, non-elastic material that may be reinforced with fibers. The material of the lower portion 88 may be woven together. The lower portion 88 or at least the weakened region 91 of the lower portion 88 may include perforations along a main axis of the sheath 80—that can be penetrated by a sharp fixation element head. For example, as shown in FIG. 5, the lower portion 88 may include one or more recesses 96 that are configured to mechanically weaken the material of the lower portion 88. The lower portion 88 may also have a weakened region 91 that has a material thickness $T_B$ that is in the range of about 0.06 mm to about 0.15 mm. A typical value is about 0.1 mm.

In case of radiation-curing, the sheath 80 may be transparent to electromagnetic radiation, e.g. UV light, X-ray, or visible light. In case of moisture curing, the sheath 60 may be water-(semi) permeable. Moreover, a system that intends the use of a sheath 80 may not need a special application device, such as device 26 or 26a, to apply the hardenable material 22.

In operation and referring back to FIG. 4A, the fixation elements 14a are inserted into the bone fragments 30a, and 30b on both sides of the fracture 34. The fixation elements 14a may be inserted into the bone fragments such that the heads 46a protrude from the fragment surfaces. The hardenable material 22 while in a non-activated (liquid state) may be disposed in the sheath 80. The hardenable material 22 may then be applied by pressing the sheath 80 onto the heads 46a of the fixation elements 14a across the fracture 34. The heads 46a of the fixation elements 14a may penetrate through the lower portion 88 of the sheath 80 to thereby allow the hardenable material 22 to flow around the fixation element heads 46a. Subsequently, the hardenable material 22 is cured in situ by a suitable curing procedure (UV light, laser light, temperature or moisture) so as to polymerize and fix the hardenable material 22 and the sheath 80 to the bone fixation elements 14a, to thereby form a stabilized construct. While in the described procedure the hardenable material 22 and the sheath 80 are affixed to the bone fixation elements 14a, it should be understood that the sheath 80 may be removed after curing of the hardenable material 22. Furthermore, if the sheath 80 is made from a resorbable material, the sheath 80 may be left behind and may be resorbed.

In another embodiment, the sheath 80 is formed by the hardenable material itself. The sheath 80 is formed by exposing a top layer of the hardenable material 22 to an environment suitable for the polymerization. The sheath 80, so formed, provides an envelope around the remaining hardenable material 22.

As shown in FIGS. 6A and 6B, the systems 10 or 110 may further include a reduction instrument, such as a wire 100 to help facilitate reduction of the bone fracture. The wire 100 may be made from a biocompatible material and may be resorbable. The fracture may be reduced by pulling the fixation elements 14 together with the wire 100. Once the fracture is reduced, the hardenable material 22 may be applied and cured to increase the stability of the construct, for instance directly applied as illustrated in FIGS. 1A and 3, or via a sheath as illustrated in FIG. 4A.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art. Moreover it should be understood that the features of each embodiment may be incorporated into any of the other embodiments, and that any bone fixation element may be used with any of the bone fixation systems so long as the system can function as intended.

The invention claimed is:

1. A fixation system configured to affix a relative position between first and second anatomical bodies, the system comprising:
    a first fixation element including a first shaft that is elongate along a first central axis and a first head that extends proximally from the first shaft, wherein the first shaft is configured to be attached to the first anatomical body, and each of the first shaft and the first head define respective outer dimensions along a direction substantially perpendicular to the first central axis such that the outer dimension of the first head is greater than the outer dimension of the first shaft;
    a second fixation element including a second shaft that is elongate along a second central axis and a second head that extends proximally from the second shaft, wherein the second shaft is configured to be attached to the second anatomical body, and each of the second shaft and the second head define respective outer dimensions along a direction substantially perpendicular to the second central axis such that outer dimension of the second head is greater than the outer dimension of the second shaft;
    a sheath containing a hardenable material that is in an unhardened state, the sheath configured to be ruptured by the first fixation element such that the hardenable material flows into a first gap between the first head and an exterior surface of a first anatomical body when the first shaft is attached to the first anatomical body, the sheath further configured to be ruptured by the second fixation element such that the hardenable material flows into a second gap between the second head and an exterior surface of the second anatomical body when the second shaft is attached to the second anatomical body, wherein the hardenable material is configured to be hardened so as to join the first and second heads together, thereby fixing a relative position between the first and second anatomical bodies when the first and second shafts are attached to the first and second anatomical bodies, respectively.

2. The fixation system of claim 1, wherein the hardenable material is injectable or deformable.

3. The fixation system of claim 1, wherein the hardenable material has a viscosity that is between about 10 Pa s and about 100 Pa s.

4. The fixation system of claim 3, wherein the viscosity is between about 30 Pa s and 60 Pa s.

5. The fixation system of claim 1, wherein the hardenable material is resorbable.

6. The fixation system of claim 5, wherein the fixation elements are resorbable.

7. The fixation system of claim 1, wherein the hardenable material comprises as a base material bisphenol A diglycidyl methacrylate (Bis-GMA), diglycidylmethacrylate (DGMA), triethyleneglycoldimethacrylate (TEGDMA), urethane dimethacrylate (UDMA), 1,10-decanediol dimethacrylate, 2-hydroxyethylmethacrylate, 2-hydroxypropylmethacrylate, ethylene glycol dimethacrylate, diethylene glycol dimethacrylate, tetraethylene glycol dimethacrylate, 1,6-hexamethylene diisocyanate, 1,6-hexanedioldimethacrylate, acryl- or methacryl-based formulations (non-resorbable), vinylester-, vinylcarbonate-, vinylcarbamate-based (resorbable), PCL, PCL/TCP, PCL/HA, polyurethane or any of these materials reinforced with fibers or particles comprising Mg, PLA, calciumphosphate ceramic (e.g. beta-tricalciumphosphate (TCP) or hydroxyapatite (HA)).

8. The fixation system of claim 7, wherein the hardenable material further comprises one or more thiol-ene derivates.

9. The fixation system of claim 7, wherein the hardenable material further comprises photoinitiators, camphorquinone, any ketone, or alpha-diketone compounds.

10. The fixation system of claim 7, wherein the hardenable material contains one or more additives, wherein the additive is one or more of an anti-inflammatory agent, an antibacterial agent, an antifungal agent, an anti-viral agent, an analgesic or an osteoinductive agent.

11. The fixation system of claim 1, wherein the first and second shafts are configured to be inserted into the first and second anatomical bodies, respectively.

12. A fixation system configured to affix a relative position between first and second anatomical bodies, the system comprising:
    a first fixation element configured to be affixed to a first anatomical body;
    a second fixation element configured to be affixed to a second anatomical body;
    a hardenable material; and
    a sheath defining a cavity that retains the hardenable material in a non-activated state, wherein the sheath defines a bone-facing surface that includes at least one region configured to abut at least one of the first and second fixation elements, wherein the at least one of the first and second fixation elements is configured to rupture the region when pressure is applied to the sheath so as to cause the hardenable material to flow from the cavity through the bone-facing surface and to the first and second fixation elements,
    wherein the hardenable material is configured to be hardened so as to join the first and second fixation elements together, thereby fixing a relative position between the first and second fixation elements.

13. The fixation system of claim 12, wherein the sheath has a height that is between about 2 mm and about 3 mm.

14. The fixation system of claim 12, wherein the at least one region is a weakened region.

15. The fixation system of claim 14, wherein the weakened region has a material thickness that is between about 0.06 mm to about 0.15 mm.

16. The fixation system of claim 14, wherein the weakened region comprises a cellulose or silk based material.

17. The fixation system of claim 14, wherein the weakened region comprises one or more recesses.

18. The fixation system of claim 12, wherein the sheath includes an upper portion that is made from a transparent elastomer material.

19. The fixation system of claim 18, wherein the upper portion consists of a polymerized layer of the hardenable material.

20. The fixation system of claim 12, wherein each of the at least two bone fixation elements includes a shaft and a head that extends proximally from the shaft, the shaft having a first dimension and is configured to be implanted into one of the bone fragments, the head having a second dimension that is greater than the first dimension and is configured to be anchored in the hardenable material.

21. The fixation system of claim 20, wherein the head defines a passageway that is configured to receive the hardenable material.

22. The fixation system of claim 20, wherein the head defines a proximal tip.

* * * * *